US012648922B2

(12) United States Patent (10) Patent No.: US 12,648,922 B2

Jewell et al. (45) Date of Patent: Jun. 9, 2026

(54) PET FOOD COMPOSITIONS, METHOD OF TREATING AN INFLAMMATORY CONDITION AND METHOD OF REDUCING CICULATPRO-INFLAMMATORY CYTOKINES

(71) Applicant: Hill's Pet Nutrition, Inc., Topeka, KS (US)

(72) Inventors: Dennis Jewell, Lawrence, KS (US); Kiran Panickar, Lawrence, KS (US)

(73) Assignee: Hill's Pet Nutrition, Inc., Overland Park, KS (US)

( * ) Notice: Subject to any disclaimer, the term of this patent is extended or adjusted under 35 U.S.C. 154(b) by 997 days.

(21) Appl. No.: 17/309,122

(22) PCT Filed: Nov. 2, 2018

(86) PCT No.: PCT/US2018/059001

§ 371 (c)(1),
(2) Date: Apr. 27, 2021

(87) PCT Pub. No.: WO2020/091813

PCT Pub. Date: May 7, 2020

(65) Prior Publication Data

US 2022/0000826 A1 Jan. 6, 2022

(51) Int. Cl.
| | |
|---|---|
| *A61K 31/202* | (2006.01) |
| *A23K 10/30* | (2016.01) |
| *A23K 20/158* | (2016.01) |
| *A23K 50/40* | (2016.01) |
| *A61K 9/00* | (2006.01) |
| *A61K 36/48* | (2006.01) |
| *A61K 36/53* | (2006.01) |
| *A61K 36/82* | (2006.01) |
| *A61P 37/06* | (2006.01) |

(52) U.S. Cl.
CPC ............ *A61K 31/202* (2013.01); *A23K 10/30* (2016.05); *A23K 20/158* (2016.05); *A23K 50/40* (2016.05); *A61K 9/0056* (2013.01); *A61K 36/48* (2013.01); *A61K 36/53* (2013.01); *A61K 36/82* (2013.01); *A61P 37/06* (2018.01)

(58) Field of Classification Search
CPC ........ A61K 36/82; A61K 36/48; A61K 36/53; A23K 50/40; A23K 10/30; A23K 20/158
See application file for complete search history.

(56) References Cited

U.S. PATENT DOCUMENTS

| | | | |
|---|---|---|---|
| 6,926,917 | B2 | 8/2005 | Parthasarathy |
| 10,245,296 | B2 | 4/2019 | Khoo et al. |
| 10,406,232 | B2 | 9/2019 | DuBourdieu et al. |
| 2005/0266051 | A1 | 12/2005 | Kelley et al. |
| 2010/0021573 | A1* | 1/2010 | Gonzalez ............. A61K 31/714 |
| | | | 424/766 |
| 2011/0104327 | A1 | 5/2011 | Kirejevas |
| 2011/0206721 | A1* | 8/2011 | Nair ........................ A61P 29/00 |
| | | | 424/195.15 |
| 2013/0059057 | A1* | 3/2013 | Mizuuchi ............... A23K 20/30 |
| | | | 426/601 |
| 2014/0287071 | A1 | 9/2014 | Barnett, III |
| 2017/0119841 | A1 | 5/2017 | Mathias et al. |
| 2017/0143009 | A1* | 5/2017 | Awati ..................... A23K 40/30 |
| 2020/0120956 | A1 | 4/2020 | Jewell |

FOREIGN PATENT DOCUMENTS

| | | |
|---|---|---|
| JP | 2005-533864 A | 11/2005 |
| JP | 2013-515500 A | 5/2013 |
| WO | 2001/082720 | 11/2001 |
| WO | 2014/149434 | 9/2014 |
| WO | WO-2017058291 A1 * 4/2017 ............. A23K 10/20 |
| WO | 2018/125029 | 7/2018 |

OTHER PUBLICATIONS

Holub, CMAJ, 166(5), 2002, 608-615.*
Merriam-Webster 'botanical', 1 page.*
International Search Report and the Written Opinion of the International Searching Authority issued in International Application PCT/US2018/059001 mailed Jun. 27, 2019.

* cited by examiner

*Primary Examiner* — Kyle A Purdy

(57) ABSTRACT

Described herein are pet food compositions for reducing circulating pro-inflammatory cytokines in companion animals. Methods of making and using the same are also described.

9 Claims, No Drawings

PET FOOD COMPOSITIONS, METHOD OF TREATING AN INFLAMMATORY CONDITION AND METHOD OF REDUCING CICULATPRO-INFLAMMATORY CYTOKINES

BACKGROUND

Companion animals, especially cats, suffer from a number of diseases in which inflammation plays a significant role including cystitis, gastritis, arthritis. Additionally, inflammation has a significant but in a secondary role other diseases and conditions such as obesity.

Prior research on humans and other mammals have shown that certain long-chained omega-6 fatty acids, such as arachidonic acid, have pro-inflammatory properties. Arachidonic acid is metabolized to both pro-inflammatory and anti-inflammatory eicosanoids during and after the inflammatory response, respectively. Arachidonic acid is also metabolized to inflammatory and anti-inflammatory eicosanoids during and after physical activity to promote growth.

Prior research on humans and other mammals have also shown that specific botanicals have anti-inflammatory properties.

A method of improving the level of hydration in a cat is disclosed in U.S. Pat. No. 9,884,035. Cats fed diets containing certain amounts and ratios of arachidonic acid and eicosapentaenoic acid are sufficiently hydrated and at reduced risk for development of urinary stones, feline idiopathic cystitis, or FLUTD.

A composition and a method for reducing or treating oral inflammation is taught in Int'l Patent Publication No. WO/2016/099477. A method of reducing or treating oral inflammation in an animal, comprising feeding the animal primarily disc-shaped food kibbles comprising one or more botanicals, wherein a reduction of oral inflammation is achieved in the animal after or during ingestion of the disc-shaped kibbles is disclosed. That publication also discloses a food kibble comprising one or more botanicals, wherein the food kibble has primarily a disc shape and reduces oral inflammation in an animal when the animal ingests the food kibble.

A composition that includes ginger for the amelioration or prevention of inflammatory conditions is taught in U.S. Patent Publication 2017/0239314. Pet food compositions for a companion animal includes an effective amount of ginger to prevent, to ameliorate the symptoms of or to treat, inflammation or an inflammatory disorders in the companion animal, where the inflammation or inflammatory disorder is an arthritic condition or a gastrointestinal disorder. The arthritic condition may be osteoarthritis, rheumatoid arthritis, psoriatic arthritis, ankylosing spondylitis or a local inflammatory joint condition. Gastrointestinal disorders may include irritable bowel disorders and chronic diarrhea.

A method of control and prophylaxis of inflammation and mitigation of inflammatory conditions in companion animals is taught in U.S. Patent Application Publication No. 2013/0041020. A method of control and prophylaxis of inflammation and mitigation of inflammatory conditions, particularly arthritis and joint pain, in companion animals, e.g., dogs or cats, comprises administering a diet comprising lipoic acid for a period of at least two weeks, wherein the diet comprises a food having 10-10,000 ppm of lipoic acid, e.g., a dry food, comprising 50-200 ppm lipoic acid. The companion animal diet contains lipoic acid, e.g., for a period of at least two weeks, e.g., wherein the diet comprises a food having 10-10,000 ppm of lipoic acid, e.g., a dry food comprising 50-200 ppm lipoic acid, to reduce expression of one or more of the biomarkers for inflammation.

Although many advances in the art of formulating cat food compositions have been made with respect to treating inflammation, many more challenges remain, due to the cats unique metabolism, compared to those of other mammals, including humans. The cat has a reduced ability to desaturate and elongate essential fatty acids when compared to other mammals, thus has a very limited capacity to convert linoleic acid to arachidonic acid, making it an essential part of their diets.

BRIEF SUMMARY

In some embodiments, the present invention relates to a dietary composition for reducing circulating pro-inflammatory cytokines in companion animals. The present invention is related to the composition of a combination of botanicals and $C_{20+}$ polyunsaturated fatty acid in a dietary composition, and to the use of such composition to reduce circulating pro-inflammatory cytokines in companion animals.

The efficacy of anti-inflammatory substance, such as pet food, may be measured directly by monitoring inflammation. Alternatively, the efficacy of anti-inflammatory substance may be measured by the reduction of selected circulating pro-inflammatory cytokines in the companion animal. Suitable pro-inflammatory cytokines include TNFα, MCP-1, IL12 and IL18.

Feeding cats a combination of arachidonic acid and botanicals in pet food has shown very significant anti-inflammatory effect as exhibited by the reduction of TNFα, MCP-1, and IL-18.

In other embodiments, the present invention is also directed to a dietary composition for a companion animal comprising greater than about 0.10 wt % of polyunsaturated fatty acid comprising 20 or more carbons; and a botanical; wherein all wt % are with respect to the dietary composition on a dry matter basis.

Examples of polyunsaturated fatty acid comprising 20 or more carbons include methylene-interrupted polyenes, polyunsaturated omega-3 fatty acids, polyunsaturated omega-6 fatty acids, polyunsaturated omega-9 fatty acids, Additional examples of omega-3 fatty acids with 20 or more carbons include eicosatrienoic acid, eicosatetraenoic acid, eicosapentaenoic acid, heneicosapentaenoic acid, docosapentaenoic acid, docosahexaenoic acid, tetracosapentaenoic acid, tetracosahexaenoic acid, and mixtures thereof, wherein for each of the acids the double bonds can be anywhere in the chain as long as the last double bond is between the third and fourth carbon from the omega end of the fatty acid, and wherein each of the double bonds in each of the acids may be either cis or trans.

Examples of omega-6 fatty acids with 20 or more carbons include eicosadienoic acid, eicosatrienoic acid, eicosatetraenoic acid, docosadienoic acid, docosatrienoic acid, docosatetraenoic acid, docosapentaenoic acid, tetracosadienoic acid, tetracosadienoic acid, tetracosatetraenoic acid, tetracosapentaenoic acid, and mixtures thereof, wherein for each of the acids the double bonds can be anywhere in the chain as long as the last double bond is between the sixth and seventh carbon from the omega end of the fatty acid.

Under one embodiment, the present invention is directed to a dietary composition for a companion animal comprising: greater than about 0.10 wt % of polyunsaturated fatty acid selected from the group consisting of eicosadienoic acid, eicosatrienoic acid, eicosatetraenoic acid, docosadienoic acid, docosatetraenoic acid, docosapentaenoic acid, tetracosatetraenoic acid, tetracosapentaenoic acid, and mixtures thereof; and a botanical.

Arachidonic acid is a specific isomer of eicosatetraenoic acid, namely (5Z,8Z,11Z,14Z)-eicosa-5,8,11,14-tetraenoic acid. It is a polyunsaturated omega-6 fatty acid, with the formula $CH_3$—$(CH_2)_4$—$(CH=CH—CH_2)_4$—$(CH_2)_2$—COOH), wherein all double bonds are cis.

Examples of a botanical include substances derived from the group consisting of licorice root, *angelica* root, fenugreek, marigold, fennel, peppermint leaf, chamomile, dandelion, savory, green tea, tulsi, basil, alfalfa, parsley, fennel, goldenseal, and mixtures thereof.

The composition of the invention can be a liquid or a solid food. Where the composition is a solid, the polyunsaturated fatty acid comprising 20 or more carbons, and the botanical, may be coated on the composition, or incorporated into the composition or both.

Under one embodiment, the present invention is directed to a dietary composition for a companion animal comprising greater than about 0.10 wt % of polyunsaturated fatty acid comprising 20 or more carbons; and a botanical, wherein the botanical is selected from the group consisting of green tea, fenugreek, tulsi, and mixtures thereof. Under one embodiment, all three botanicals are necessarily present in dietary composition.

The green tea, fenugreek, and tulsi may be present in any amount that is effective in treating inflammation in a companion animal. Under one embodiment each of the green tea, fenugreek, and tulsi is present in the composition at greater than about 0.0010 wt %. Under one embodiment the dietary composition comprises greater than about 0.20 wt % green tea, greater than about 0.020 wt % fenugreek, and greater than about 0.0010 wt % tulsi.

The invention is defined by at least twenty aspects.

In the first aspect, the invention relates to a dietary composition for a companion animal comprising: (a) greater than about 0.10 wt % of polyunsaturated fatty acid comprising 20 or more carbons; and (b) a botanical, wherein all wt % are with respect to the dietary composition on a dry matter basis.

In the second aspect, the invention relates to a dietary composition for a companion animal comprising: (a) greater than about 0.10 wt % of polyunsaturated fatty acid comprising 20 or more carbons selected from the group consisting of omega-3 fatty acid, omega-6 fatty acid, omega-9 fatty acid, and mixtures thereof; and (b) a botanical, wherein all wt % are with respect to the dietary composition on a dry matter basis.

In the third aspect, the invention relates to a dietary composition for a companion animal comprising: (a) greater than about 0.10 wt % of polyunsaturated fatty acid comprising 20 or more carbons selected from the group consisting of eicosadienoic acid, eicosatrienoic acid, eicosatetraenoic acid, docosadienoic acid, docosatetraenoic acid, docosapentaenoic acid, tetracosatetraenoic acid, tetracosapentaenoic acid, and mixtures thereof; and (b) a botanical, wherein all wt % are with respect to the dietary composition on a dry matter basis.

In the fourth aspect, the invention relates to a dietary composition for a companion animal comprising: (a) greater than about 0.10 wt % of polyunsaturated fatty acid comprising 20 or more carbons and 4 or more carbon-carbon double bonds; and (b) a botanical, wherein all wt % are with respect to the dietary composition on a dry matter basis.

In the fifth aspect, the invention relates to a dietary composition for a companion animal comprising: (a) greater than about 0.10 wt % of polyunsaturated fatty acid comprising 20 or more carbons and 4 or more carbon-carbon double bonds selected from the group consisting of eicosatetraenoic acid, eicosapentaenoic acid, heneicosapentaenoic acid, docosatetraenoic acid, docosapentaenoic acid, docosahexaenoic acid, tetracosatetraenoic acid, tetracosapentaenoic acid, tetracosahexaenoic acid, arachidonic acid, and mixtures thereof; and (b) a botanical, wherein all wt % are with respect to the dietary composition on a dry matter basis.

In the sixth aspect, the invention relates to a dietary composition for a companion animal comprising: (a) greater than about 0.10 wt % of polyunsaturated fatty acid comprising 20 or more carbons comprising arachidonic acid; and (b) a botanical, wherein all wt % are with respect to the dietary composition on a dry matter basis.

In the seventh aspect, the invention relates to a dietary composition for a companion animal comprising: (a) greater than about 0.20 wt % of polyunsaturated fatty acid comprising 20 or more carbons; and (b) a botanical, wherein all wt % are with respect to the dietary composition on a dry matter basis.

In the eighth aspect, the invention relates to a dietary composition for a companion animal comprising: (a) greater than about 0.10 wt % of polyunsaturated fatty acid comprising 20 or more carbons; and (b) a botanical selected from the group consisting of licorice root, *angelica* root, fenugreek, marigold, fennel, peppermint leaf, chamomile, dandelion, savory, green tea, tulsi, basil, alfalfa, parsley, goldenseal, and mixtures thereof, wherein all wt % are with respect to the dietary composition on a dry matter basis.

In the ninth aspect, the invention relates to a dietary composition for a companion animal comprising: (a) greater than about 0.10 wt % of polyunsaturated fatty acid comprising 20 or more carbons; and (b) a botanical elected from the group consisting of green tea, fenugreek, tulsi, and mixtures thereof, wherein all wt % are with respect to the dietary composition on a dry matter basis.

In the tenth aspect, the invention relates to a dietary composition for a companion animal comprising: (a) greater than about 0.10 wt % of polyunsaturated fatty acid comprising 20 or more carbons; and (b) a botanical comprising a mixture of green tea, fenugreek, and tulsi, wherein all wt % are with respect to the dietary composition on a dry matter basis.

In the eleventh aspect, the invention relates to a dietary composition for a companion animal comprising: (a) greater than about 0.10 wt % of polyunsaturated fatty acid comprising 20 or more carbons; and (b) a botanical comprising a mixture of green tea, fenugreek, and tulsi, wherein each of the green tea, fenugreek, and tulsi is present in the composition at greater than about 0.0010 wt %; wherein all wt % are with respect to the dietary composition on a dry matter basis.

In the twelfth aspect, the invention relates to a dietary composition for a companion animal comprising: (a) greater than about 0.10 wt % of polyunsaturated fatty acid comprising 20 or more carbons; and (b) a botanical comprising a mixture of green tea, fenugreek, and tulsi, comprising greater than about 0.20 wt % green tea, greater than about 0.020 wt % fenugreek, and greater than about 0.0010 wt % tulsi, wherein all wt % are with respect to the dietary composition on a dry matter basis.

In the thirteenth aspect, the invention relates to a dietary composition for a companion animal comprising: (a) greater than about 0.10 wt % of polyunsaturated fatty acid comprising 20 or more carbons; and (b) a botanical, wherein all wt % are with respect to the dietary composition on a dry matter basis, wherein the dietary composition comprises a nutritionally complete pet food.

In the fourteenth aspect, the invention relates to a dietary composition for a companion animal comprising: (a) greater than about 0.10 wt % of polyunsaturated fatty acid comprising 20 or more carbons; and (b) a botanical, wherein all wt % are with respect to the dietary composition on a dry matter basis, wherein the dietary composition comprises a nutritionally complete cat food.

In the fifteenth aspect, the invention relates to a dietary composition for a companion animal comprising: (a) greater than about 0.10 wt % of polyunsaturated fatty acid comprising 20 or more carbons; and (b) a botanical, wherein all wt % are with respect to the dietary composition on a dry matter basis, wherein the dietary composition is a dry composition.

In the sixteenth aspect, the invention relates to a dietary composition for a companion animal comprising: (a) greater than about 0.10 wt % of polyunsaturated fatty acid comprising 20 or more carbons; and (b) a botanical, wherein all wt % are with respect to the dietary composition on a dry matter basis, wherein the companion animal is a cat.

In the seventeenth aspect, the invention relates to a dietary composition for a companion animal comprising epigallo-catechin-3-gallate, and greater than about 0.10 wt % of arachidonic acid.

In the eighteenth aspect, the invention relates to a method of reducing circulating pro-inflammatory cytokines in a companion animal in need thereof comprising providing the companion animal with a dietary composition comprising an effective amount of polyunsaturated fatty acid comprising 20 or more carbons and a botanical.

In the nineteenth aspect, the invention relates to a method of reducing circulating pro-inflammatory cytokines in a companion animal in need thereof comprising providing the companion animal with a dietary composition comprising an effective amount of polyunsaturated fatty acid comprising 20 or more carbons and comprises 4 or more carbon-carbon double bonds, and a botanical.

In the twentieth aspect, the invention relates to a method of reducing circulating pro-inflammatory cytokines in a companion animal in need thereof comprising providing the companion animal with a dietary composition comprising an effective amount of polyunsaturated fatty acid comprising 20 or more carbons and a botanical, wherein the dietary composition comprises a nutritionally complete cat food.

DETAILED DESCRIPTION

For illustrative purposes, the principles of the present invention are described by referencing various exemplary embodiments thereof. Although certain embodiments of the invention are specifically described herein, one of ordinary skill in the art will readily recognize that the same principles are equally applicable to, and can be employed in other apparatuses and methods. Before explaining the disclosed embodiments of the present invention in detail, it is to be understood that the invention is not limited in its application to the details of any particular embodiment shown. The terminology used herein is for the purpose of description and not of limitation.

As used herein and in the appended claims, the singular forms "a", "an", and "the" include plural references unless the context clearly dictates otherwise. The singular form of any class of the ingredients refers not only to one chemical species within that class, but also to a mixture of those chemical species; for example, the term "omega-6 fatty acid" in the singular form, may refer to a mixture of compounds each of which is also an omega-6 fatty acid. The singular form of the ingredient defined as a "botanical" may also be a mixture of ingredients each of which may be defined as a botanical. The terms "a" (or "an"), "one or more" and "at least one" may be used interchangeably herein. The terms "comprising", "including", and "having" may be used interchangeably.

The abbreviations and symbols as used herein, unless indicated otherwise, take their ordinary meaning. The abbreviation "wt %" means percent by weight. The abbreviation "LS(mean)" is a statistical least square means. The characters "α", "β", "γ", "@", and "Δ" are Greek letters alpha, beta, gamma, omega, and capital delta, respectively. When referring to chemical structures, and names, the symbols "C", "H", and "O" mean carbon, hydrogen, and oxygen, respectively. The symbols "Z", "E", "-", and "=" mean cis, trans, single bond, and double bond, respectively.

The term "about" when referring to a number means±5%. For example, the phrase "about 0.050 wt %" refers to a number between and including 0.047500 wt % and 0.052500 wt %.

As used throughout, ranges are used as shorthand for describing each and every value that is within the range. Any value within the range can be selected as the terminus of the range.

Selected terms recited below may be used as more than one parts of speech. For example, the term "botanical" may be used as a noun or as an adjective.

The term "mixture" is to be interpreted broadly. When referring to a list of ingredients, unless specifically indicated otherwise, the term "mixture" refers to a mixture of the aforementioned ingredients with each other, a mixture of any of aforementioned ingredients with other ingredients that are not aforementioned, and to a mixture of several aforementioned ingredients with other ingredients that are not aforementioned. For example, the term "mixture" in the phrase "the polyunsaturated fatty acid is selected from the group consisting of omega-3 fatty acid, omega-6 fatty acid, omega-9 fatty acid, and mixtures thereof" refers to a mixture of omega-3 fatty acid and omega-6 fatty acid; or a mixture of omega-3 fatty acid and omega-9 fatty acid; or a mixture of omega-6 fatty acid and omega-9 fatty acid; or a mixture of omega-3 fatty acid, omega-6 fatty acid, omega-9 fatty acid; or a mixture of omega-3 fatty acid and any other the polyunsaturated fatty acid; or a mixture of omega-3 fatty acid and any other the polyunsaturated fatty acid; or a mixture of omega-6 fatty acid and any other the polyunsaturated fatty acid; or a mixture of omega-9 fatty acid and any other the polyunsaturated fatty acid; or a mixture of omega-3 fatty acid, omega-6 fatty acid, and any other the polyunsaturated fatty acid; or a mixture of omega-3 fatty acid, omega-9 fatty acid, and any other the polyunsaturated fatty acid; or a mixture of omega-6 fatty acid, omega-9 fatty acid, and any other the polyunsaturated fatty acid; or a mixture of omega-3 fatty acid, omega-6 fatty acid, omega-9 fatty acid, and any other the polyunsaturated fatty acid. For each of these, the phrase "any other the polyunsaturated fatty acid" means one or more polyunsaturated fatty acid besides omega-3 fatty acid, omega-6 fatty acid, or omega-9 fatty acid.

Any member in a list of species that are used to exemplify or define a genus, may be mutually different from, or overlapping with, or a subset of, or equivalent to, or nearly the same as, or identical to, any other member of the list of species. Further, unless explicitly stated, such as when reciting a Markush group, the list of species that define or exemplify the genus is open, and it is given that other species may exist that define or exemplify the genus just as well as, or better than, any other species listed.

The phrase "a companion animal" refers to a domesticated or domestic-bred animal whose physical, emotional, behavioral and social needs can be readily met as companions in a home, or in close daily relationship with one or more humans. Under one embodiment, species included in the definition of a companion animal include dogs, cats, horses, rabbits, ferrets, guinea pigs and select other small mammals. Under another embodiment, species included in the definition of a companion animal include dogs, cats, horses, rabbits, ferrets, guinea pigs and select other small mammals, birds, small reptiles, fish, and domestic-bred farm animals.

The definition of the term "cat" includes a domestic cat, *Felis catus*, and *Felis silvestris catus*. The definition of the term cat includes a house cat and a feral cat. The definition of the term cat includes breeds such as Abyssinian, Aegean, American Curl, American Bobtail, American Shorthair, American Wirehair, Aphrodite Giant, Arabian Mau, Australian Mist, Asian, Asian Semi-longhair, Balinese, Bambino, Bengal, Birman, Bombay, Brazilian Shorthair, British Angora, British Semi-longhair, British Shorthair, British Longhair, Burmese, Burmilla, California Spangled, Chantilly-Tiffany, Chartreux, Chausie, Cheetoh, Colorpoint Shorthair, Colorpoint Persian, Cornish Rex, Cymric, Cyprus, Devon Rex, Donskoy, Don Sphynx, Dragon Li, Dwelf, Egyptian Mau, European Shorthair, Exotic Shorthair, Foldex, Foreign Longhair, German Rex, Havana Brown, Highlander, Himalayan, Japanese Bobtail, Javanese, Karelian Bobtail, Khao Manee, Korat, Korean Bobtail, Korn Ja, Kurilian Bobtail, Kuril Islands Bobtail, LaPerm, Liebling, Longhaired Manx, Lykoi, Maine Coon, Mandarin, Manx, Manx Longhair, Mekong Bobtail, Minskin, Munchkin, Nebelung, Napoleon, Norwegian Forest, Ocicat, Ojos Azules, Oregon Rex, Oriental Bicolor, Oriental Shorthair, Oriental Longhair, Persian, Peterbald, Pixie-bob, Raas, Ragamuffin, Ragdoll, Russian Blue, Russian Black, Russian Tabby, Russian White, Sam Sawet, Savannah, Scottish Fold, Selkirk Rex, Serengeti, Serrade petit, Siamese, Siberian, Siberian Forest, Neva Masquerade, Singapura, Snowshoe, Sokoke, Somali, Sphynx, Suphalak, Thai, Thai Lilac, Tonkinese, Toyger, Turkish Angora, Turkish Van, Ukrainian Levkoy, Wichien Maat, Wila Krungthep, and York Chocolate.

The phrase "dietary composition" refers to food for consumption by a companion animal, or to food for consumption by a cat. This phrase is to be interpreted broadly; the phrase includes food that is consumed by the companion animal or by the cat on exclusive basis, food that is consumed by the companion animal or by the cat regular basis, food by the companion animal or by the cat consumer on occasional basis, and food by the companion animal or by the cat consumer on rare basis.

The present invention is directed to a dietary composition for reducing circulating pro-inflammatory cytokines in companion animals.

The present invention is related to the composition of a combination of botanicals and $C_{20+}$ polyunsaturated fatty acid in a dietary composition, and to the use of such composition to reduce circulating pro-inflammatory cytokines in companion animals.

Under one embodiment, the present invention is directed to a dietary composition for a companion animal comprising greater than about 0.10 wt % of polyunsaturated fatty acid comprising 20 or more carbons; and a botanical; wherein all wt % are with respect to the dietary composition on a dry matter basis.

The dietary composition of the present invention comprises a polyunsaturated fatty acid that contains 20 or more carbon atoms.

Polyunsaturated fatty acid is a fatty acid that comprises two or more carbon-carbon double bonds in the carbon chain. A fatty acid is a carboxylic acid with a long aliphatic chain. Polyunsaturated fatty acid has the formula $CH_3$—$[(CH_2)_m$—$(CH=CH)_n]_o$—$COOH$, wherein variables m, n, and o are non-negative integers 0, 1, 2, . . . .

Examples of polyunsaturated fatty acid comprising 20 or more carbons include methylene-interrupted polyenes, polyunsaturated omega-3 fatty acids, polyunsaturated omega-6 fatty acids, and polyunsaturated omega-9 fatty acids. These fatty acids may be contained in triacylglycerides, phosphatidyl cholines, and phosphatidyl ethanolamines.

The definition of polyunsaturated fatty acid comprising 20 or more carbons specifically includes such acids which are encountered rarely. For example, although the most common omega-9 fatty acids are mono-unsaturated fatty acid, polyunsaturated omega-9 fatty acid comprising 20 or more carbons include (5Z,8Z,11Z)-docos-5,8,11-trienoic acid, (4Z,7Z,10Z,13Z)-tetracos-4,7,10,17-tetraenoic acid, and like.

Under one embodiment of the present invention, the polyunsaturated fatty acid comprising 20 or more carbons is selected from the group consisting of omega-3 fatty acid, omega-6 fatty acid, omega-9 fatty acid, and mixtures thereof.

One or more omega-3 fatty acid is important for normal metabolism of companion animals. Mammals are unable to synthesize omega-3 fatty acids, but can obtain the shorter-chain omega-3 fatty acid α-linolenic acid through diet and use it to form the more important long-chain omega-3 fatty acid eicosapentaenoic acid and docosahexaenoic acid. The ability to make the longer-chain omega-3 fatty acids from α-linolenic acid may be impaired in aging.

Examples of omega-3 fatty acids with 20 or more carbons include eicosatrienoic acid, ETE, (11Z,14Z,17Z)-eicosa-11,14,17-trienoic acid, eicosatetraenoic acid, ETA, (8Z,11Z,14Z,17Z)-eicosa-8,11,14,17-tetraenoic acid, eicosapentaenoic acid, EPA, (5Z,8Z,11Z,14Z,17Z)-eicosa-5,8,11,14,17-pentaenoic acid, heneicosapentaenoic acid, HPA, (6Z,9Z,12Z,15Z18Z)-heneicosa-6,9,12,15,18-pentaenoic acid, docosapentaenoic acid, clupanodonic acid, DPA, (7Z,10Z,13Z,16Z,19Z)-docosa-7,10,13,16,19-pentaenoic acid, docosahexaenoic acid, DHA, (4Z,7Z,10Z,13Z,16Z,19Z)-docosa-4,7,10,13,16,19-hexaenoic acid, tetracosapentaenoic acid, (9Z,12Z,15Z,18Z,21Z)-tetracosa-9,12,15,18,21-pentaenoic acid, tetracosahexaenoic acid, Nisinic acid, (6Z,9Z,12Z,15Z,18Z,21Z)-tetracosa-6,9,12,15,18,21-hexaenoic acid, and mixtures thereof.

Additional examples of omega-3 fatty acids with 20 or more carbons include eicosatrienoic acid, eicosatetraenoic acid, eicosapentaenoic acid, heneicosapentaenoic acid, docosapentaenoic acid, docosahexaenoic acid, tetracosapentaenoic acid, tetracosahexaenoic acid, and mixtures thereof, wherein for each of the acids the double bonds can be anywhere in the chain as long as the last double bond is between the third and fourth carbon from the omega end of the fatty acid.

Thus, for example, examples of omega-3 fatty eicosatrienoic acid include eicosa-2,4,17-trienoic acid; eicosa-2,5,17-trienoic acid; eicosa-2,6,17-trienoic acid; eicosa-2,7,17-trienoic acid; eicosa-2,8,17-trienoic acid; eicosa-2,9,17-trienoic acid; eicosa-2,10,17-trienoic acid; eicosa-2,11,17-trienoic acid; eicosa-2,12,17-trienoic acid; eicosa-2,13,17-trienoic acid; eicosa-2,14,17-trienoic acid; eicosa-2,15,17-trienoic acid; eicosa-3,5,17-trienoic acid; eicosa-3,6,17-trienoic acid; eicosa-3,7,17-trienoic acid; eicosa-3,8,17-trienoic acid; eicosa-3,9,17-trienoic acid; eicosa-3,10,17-trienoic acid; eicosa-3,11,17-trienoic acid; eicosa-3,12,17-trienoic acid; eicosa-3,13,17-trienoic acid; eicosa-3,14,17-trienoic acid; eicosa-3,15,17-trienoic acid; eicosa-4,6,17-trienoic acid; eicosa-4,7,17-trienoic acid; eicosa-4,8,17-trienoic acid; eicosa-4,9,17-trienoic acid; eicosa-4,10,17-trienoic acid; eicosa-4,11,17-trienoic acid; eicosa-4,12,17-trienoic acid; eicosa-4,13,17-trienoic acid; eicosa-4,14,17-trienoic acid; eicosa-4,15,17-trienoic acid; eicosa-5,7,17-trienoic acid; eicosa-5,8,17-trienoic acid; eicosa-5,9,17-trienoic acid; eicosa-5,10,17-trienoic acid; eicosa-5,11,17-trienoic acid; eicosa-5,12,17-trienoic acid; eicosa-5,13,17-trienoic acid; eicosa-5,14,17-trienoic acid; eicosa-5,15,17-trienoic acid; eicosa-6,8,17-trienoic acid; eicosa-6,9,17-trienoic acid; eicosa-6,10,17-trienoic acid; eicosa-6,11,17-trienoic acid; eicosa-6,12,17-trienoic acid; eicosa-6,13,17-trienoic acid; eicosa-6,14,17-trienoic acid; eicosa-6,15,17-trienoic acid; eicosa-7,9,17-trienoic acid; eicosa-7,10,17-trienoic acid; eicosa-7,11,17-trienoic acid; eicosa-7,12,17-trienoic acid; eicosa-7,13,17-trienoic acid; eicosa-7,14,17-trienoic acid; eicosa-7,15,17-trienoic acid; eicosa-8,10,17-trienoic acid; eicosa-8,11,17-trienoic acid; eicosa-8,12,17-trienoic acid; eicosa-8,13,17-trienoic acid; eicosa-8,14,17-trienoic acid; eicosa-8,15,17-trienoic acid; eicosa-9,11,17-trienoic acid; eicosa-9,12,17-trienoic acid; eicosa-9,13,17-trienoic acid; eicosa-9,14,17-trienoic acid; eicosa-9,15,17-trienoic acid; eicosa-10,12,17-trienoic acid; eicosa-10,13,17-trienoic acid; eicosa-10,14,17-trienoic acid; eicosa-10,15,17-trienoic acid; eicosa-11,13,17-trienoic acid; eicosa-11,14,17-trienoic acid; eicosa-11,15,17-trienoic acid; eicosa-12,14,17-trienoic acid; eicosa-12,15,17-trienoic acid; and eicosa-13,15,17-trienoic acid.

Additional examples of omega-3 fatty acids with 20 or more carbons include eicosatrienoic acid, eicosatetraenoic acid, eicosapentaenoic acid, heneicosapentaenoic acid, docosapentaenoic acid, docosahexaenoic acid, tetracosapentaenoic acid, tetracosahexaenoic acid, and mixtures thereof, wherein for each of the acids the double bonds can be anywhere in the chain as long as the last double bond is between the third and fourth carbon from the omega end of the fatty acid, and wherein each of the double bonds in each of the acids may be either cis or trans.

Thus, for example, the definition of the phrase "eicosa-11,14,17-trienoic acid" includes (11Z,14Z,17Z)-eicosa-11,14,17-trienoic acid, (11E,14Z,17Z)-eicosa-11,14,17-trienoic acid, (11Z,14E,17Z)-eicosa-11,14,17-trienoic acid, (11Z,14Z,17E)-eicosa-11,14,17-trienoic acid, (11E,14E,17Z)-eicosa-11,14,17-trienoic acid, (11E,14E,17E)-eicosa-11,14,17-trienoic acid, (11Z,14E,17E)-eicosa-11,14,17-trienoic acid, (11E,14E,17E)-eicosa-11,14,17-trienoic acid, and mixtures of any of the recited acids with each other.

An omega-6 fatty acid is a polyunsaturated fatty acid wherein the final carbon-carbon double bond is in the n−6 position, i.e., the sixth bond counting from the omega end.

An omega-6 fatty acid may have pro-inflammatory or anti-inflammatory effects. The biological effects of an omega-6 fatty acid is largely produced during and after physical activity for the purpose of promoting growth and during the inflammatory cascade to halt cell damage and promote cell repair by their conversion to omega-6 eicosanoid that binds to any one of diverse receptors found in every tissue of the body.

Examples of omega-6 fatty acids with 20 or more carbons include eicosadienoic acid, (11Z,14Z)-eicosa-11,14-dienoic acid, dihomo-gamma-linolenic acid, DGLA, (8Z,11Z,14Z)-eicosa-8,11,14-trienoic acid, arachidonic acid, AA, ARA, (5Z,8Z,11Z,14Z)-eicosa-5,8,11,14-tetraenoic acid, docosadienoic acid, (13Z,16Z)-docosa-13,16-dienoic acid, adrenic acid, (7Z,10Z,13Z,16Z)-docosa-7,10,13,16-tetraenoic acid, osbond acid, (4Z,7Z,10Z,13Z,16Z)-docosa-4,7,10,13,16-pentaenoic acid, tetracosatetraenoic acid, (9Z,12Z,15Z,18Z)-tetracosa-9,12,15,18-tetraenoic acid, tetracosapentaenoic acid, and (6Z,9Z,12Z,15Z,18Z)-tetracosa-6,9,12,15,18-pentaenoic acid.

Additional examples of omega-6 fatty acids with 20 or more carbons include eicosadienoic acid, eicosatrienoic acid, eicosatetraenoic acid, docosadienoic acid, docosatrienoic acid, docosatetraenoic acid, docosapentaenoic acid, tetracosadienoic acid, tetracosadienoic acid, tetracosatetraenoic acid, tetracosapentaenoic acid, and mixtures thereof, wherein for each of the acids the double bonds can be anywhere in the chain as long as the last double bond is between the sixth and seventh carbon from the omega end of the fatty acid.

Thus, for example, examples of omega-6 fatty eicosatrienoic acid include eicosa-2,4,14-trienoic acid; eicosa-2,5,14-trienoic acid; eicosa-2,6,14-trienoic acid; eicosa-2,7,14-trienoic acid; eicosa-2,8,14-trienoic acid; eicosa-2,9,14-trienoic acid; eicosa-2,10,14-trienoic acid; eicosa-2,11,14-trienoic acid; eicosa-2,12,14-trienoic acid; eicosa-3,5,14-trienoic acid; eicosa-3,6,14-trienoic acid; eicosa-3,7,14-trienoic acid; eicosa-3,8,14-trienoic acid; eicosa-3,9,14-trienoic acid; eicosa-3,10,14-trienoic acid; eicosa-3,11,14-trienoic acid; eicosa-3,12,14-trienoic acid; eicosa-4,6,14-trienoic acid; eicosa-4,7,14-trienoic acid; eicosa-4,8,14-trienoic acid; eicosa-4,9,14-trienoic acid; eicosa-4,10,14-trienoic acid; eicosa-4,11,14-trienoic acid; eicosa-4,12,14-trienoic acid; eicosa-5,7,14-trienoic acid; eicosa-5,8,14-trienoic acid; eicosa-5,9,14-trienoic acid; eicosa-5,10,14-trienoic acid; eicosa-5,11,14-trienoic acid; eicosa-5,12,14-trienoic acid; eicosa-6,8,14-trienoic acid; eicosa-6,9,14-trienoic acid; eicosa-6,10,14-trienoic acid; eicosa-6,11,14-trienoic acid; eicosa-6,12,14-trienoic acid; eicosa-7,9,14-trienoic acid; eicosa-7,10,14-trienoic acid; eicosa-7,11,14-trienoic acid; eicosa-7,12,14-trienoic acid; eicosa-8,10,14-trienoic acid; eicosa-8,11,14-trienoic acid; eicosa-8,12,14-trienoic acid; eicosa-9,11,14-trienoic acid; eicosa-9,12,14-trienoic acid; eicosa-10,12,14-trienoic acid, and mixtures of any of the recited acids with each other.

Additional examples of omega-6 fatty acids with 20 or more carbons include eicosadienoic acid, eicosatrienoic acid, eicosatetraenoic acid, docosadienoic acid, docosatrienoic acid, docosatetraenoic acid, docosapentaenoic acid, tetracosadienoic acid, tetracosadienoic acid, tetracosatetraenoic acid, tetracosapentaenoic acid, and mixtures thereof, wherein for each of the acids the double bonds can be anywhere in the chain as long as the last double bond is between the sixth and seventh carbon from the omega end of the fatty acid and wherein each of the double bonds in each of the acids may be either cis or trans.

Thus, for example, the definition of the phrase "eicosa-8,11,14-trienoic acid" includes (8Z,11Z,14Z)-eicosa-8,11,14-trienoic acid, (8E,11Z,14Z)-eicosa-8,11,14-trienoic acid, (8Z,11E,14Z)-eicosa-8,11,14-trienoic acid, (8Z,11Z,14E)-eicosa-8,11,14-trienoic acid, (8E,11E,14Z)-eicosa-8,11,14-trienoic acid, (8E,11Z,14E)-eicosa-8,11,14-trienoic acid, (8Z,11E,14E)-eicosa-8,11,14-trienoic acid, (8E,11E,14E)-eicosa-8,11,14-trienoic acid, and mixtures of any of the recited acids with each other.

Under one embodiment, the present invention is directed to a dietary composition for a companion animal comprising: greater than about 0.10 wt % of polyunsaturated fatty acid selected from the group consisting of eicosadienoic acid, eicosatrienoic acid, eicosatetraenoic acid, docosadienoic acid, docosatetraenoic acid, docosapentaenoic acid, tetracosatetraenoic acid, tetracosapentaenoic acid, and mixtures thereof; and a botanical.

Eicosadienoic acid is one of any isomers of a straight 20 carbon chain fatty acid comprising two double carbon-carbon bonds. Examples of eicosadienoic acid include (11Z, 14Z)-icosa-11,14-dienoic acid.

Eicosatrienoic acid is one of any isomers of a straight 20 carbon chain fatty acid comprising three double carbon-carbon bonds. Examples of eicosatrienoic acid include omega-6 isomer (8Z,11Z,14Z)-eicosa-8,11,14-trienoic acid, also known as dihomo-gamma-linolenic acid. Dihomo-gamma-linolenic acid (DGLA) is an elongation product of another omega-6 fatty acid gamma-linolenic acid (GLA). Gamma-linolenic acid is a desaturation product of yet another omega-6 fatty acid linoleic acid. Dihomo-gamma-linolenic acid is found in trace amounts in animal products. Dihomo-gamma-linolenic acid production from GLA is enhanced when high levels of alpha-linolenic acid are present, blocking the arachidonic acid pathway.

Docosadienoic acid is a 22-carbon fatty acid with two double carbon-carbon bonds. Examples of docosadienoic acid include the isomer (13Z,16Z)-docosa-13,16-dienoic acid.

Under another embodiment, the present invention is directed to a dietary composition for a companion animal comprising: greater than about 0.10 wt % of polyunsaturated fatty acid comprising 20 or more carbons, and 4 or more carbon-carbon double bonds; and a botanical.

Under yet another embodiment, the present invention is directed to a dietary composition for a companion animal comprising: greater than about 0.10 wt % of polyunsaturated fatty acid comprising 20 or more carbons and 4 or more carbon-carbon double bonds selected from the group consisting of eicosatetraenoic acid, eicosapentaenoic acid, heneicosapentaenoic acid, docosatetraenoic acid, docosapentaenoic acid, docosahexaenoic acid, tetracosatetraenoic acid, tetracosapentaenoic acid, tetracosahexaenoic acid, arachidonic acid, and mixtures thereof; and a botanical. Any of these acids may have one or more isomer forms. For example, eicosatetraenoic acid may be omega-6 isomer of eicosatetraenoic acid (such as (5Z,8Z,11Z,14Z)-eicosa-5,8, 11,14-tetraenoic acid) or omega-3 isomer of eicosatetraenoic acid (such as (8Z,11Z,14Z,17Z)-eicosa-8,11,14,17-tetraenoic acid).

Eicosatetraenoic acid is one of any isomers of a straight 20 carbon chain fatty acid comprising 4 double carbon-carbon bonds. Examples of eicosatetraenoic acid include an omega-6 fatty acid isomer (5Z,8Z,11Z,14Z)-eicosa-5,8,11, 14-tetraenoic acid, and an omega-3 fatty acid isomer (8Z, 11Z,14Z,17Z)-eicosa-8,11,14,17-tetraenoic acid. Eicosatetraenoic acid is found in green-lipped mussel and appears to act as dual inhibitor of arachidonic acid oxygenation by both the cyclooxygenase and lipoxygenase pathway.

Eicosapentaenoic acid is one of any isomers of a straight 20 carbon chain fatty acid comprising 5 double carbon-carbon bonds. Examples of eicosapentaenoic acid include an omega-3 fatty acid isomer (5Z,8Z,11Z,14Z,17Z)-eicosa-5, 8,11,14,17-pentaenoic acid, commonly known as timnodonic acid. Timnodonic acid is a polyunsaturated fatty acid that acts as a precursor for prostaglandin-3, which inhibits platelet aggregation; thromboxane-3; and leukotriene-5 eicosanoids. Timnodonic acid is both a precursor and the hydrolytic breakdown product of eicosapentaenoyl ethanolamide.

Heneicosapentaenoic acid is one of any isomers of a straight 21 carbon chain fatty acid comprising 5 double carbon-carbon bonds. Examples of heneicosapentaenoic acid include an omega-3 fatty acid isomer (6Z,9Z,12Z,15Z, 18Z)-heneicosa-6,9,12,15,18-pentaenoic acid.

Docosatetraenoic acid is a 22 carbon fatty acid with four double carbon-carbon bonds. Examples of docosatetraenoic acid include the omega-6 isomer (7Z,10Z,13Z,16Z)-docosa-7,10,13,16-tetraenoic acid, commonly known as adrenic acid. Adrenic acid is a naturally occurring polyunsaturated fatty acid formed through a 2-carbon chain elongation of arachidonic acid. Adrenic acid is one of the most abundant fatty acids in the brain during early human development. Adrenic acid is an unsaturated fatty acid that is metabolized by cells to biologically active products, such as dihomoprostaglandins, dihomo-epoxyeicosatrienoic acids, and dihomo-epoxyeicosatrienoic acid.

Docosapentaenoic acid is one of any isomers of a straight 22 carbon chain fatty acid comprising 5 double carbon-carbon bonds. Examples of eicosapentaenoic acid includes an omega-6 fatty acid isomer (4Z,7Z,10Z,13Z,16Z)-docosa-4,7,10,13,16-pentaenoic acid, commonly known as osbond acid; and omega-3 fatty acid isomer (7Z,10Z,13Z,16Z,19Z)-eicosa (7,10,13,16,19) pentaenoic acid, commonly known as clupanodonic acid. Osbond acid is formed by the stepwise elongation and desaturation of arachidonic acid to the 24 carbon polyunsaturated fatty acid intermediate and the retro-conversion of said intermediate to Osbone acid. Clupanodonic acid is an intermediary between the omega-3 isomer eicosapentaenoic acid and the omega-3 docosahexaenoic acid in a pathway in which clupanodonic acid is a precursor to said docosahexaenoic acid, and the final product can be retro-converted to clupanodonic acid.

Docosahexaenoic acid is one of any isomers of a straight 22 carbon chain fatty acid comprising six double carbon-carbon bonds. Examples of docosapentaenoic acid includes (4Z,7Z,10Z,13Z,16Z,19Z)-docosa-4,7,10,13,16,19-hexaenoic acid, commonly known as cervonic acid. Omnivores and carnivores, such as cats, primarily obtain cervonic acid from their diet. Some amounts of eicosapentaenoic and cervonic acid are possible products of α-linolenic acid metabolism in young mammals. Cervonic acid in breast milk is important for a developing young mammal.

Tetracosapentaenoic acid is one of any isomers of a straight 24 carbon chain fatty acid comprising five double carbon-carbon bonds. Examples of tetracosapentaenoic acid include omega-3 fatty acid (9Z,12Z,15Z,18Z,21Z)-docosa-9,12,15,18,21-pentanoic acid.

Tetracosahexaenoic acid is one of any isomers of a straight 24 carbon chain fatty acid comprising six double carbon-carbon bonds. Examples of tetracosahexaenoic acid include (6Z,9Z,12Z,15Z,18Z,21Z)-tetracosa-6,9,12,15,18, 21-hexaenoic acid, commonly known as Nisinic acid.

Under still another embodiment, the present invention is directed to a dietary composition for a companion animal comprising: greater than about 0.10 wt % of arachidonic acid, and a botanical.

Arachidonic acid is a specific isomer of eicosatetraenoic acid, namely (5Z,8Z,11Z,14Z)-eicosa-5,8,11,14-tetraenoic acid. It is a polyunsaturated omega-6 fatty acid, with the formula $CH_3$—$(CH_2)_4$—$(CH=CH—CH_2)_4$—$(CH_2)_2$—COOH), wherein all double bonds are cis.

Although arachidonic acid is not considered as one of the essential fatty acids for most mammals, in the cat because of the reduced elongation and desaturation activity it is essential. Also, arachidonic acid becomes essential in all mammals if there is a deficiency in linoleic acid or if there is an inability to convert linoleic acid to arachidonic acid. Some mammals lack the ability to, or have a very limited capacity to convert linoleic acid in to arachidonic acid, making it an essential part of their diets. Since little or no arachidonic acid is found in common plants, such animals are obligate carnivores; the cat is a common example having a reduced ability to desaturate essential fatty acids.

Arachidonic acid is a precursor for a proinflammatory series of prostaglandins, thromboxanes, and leukotrienes as compared to those produced from omega 3 fatty acids. Virtually all cellular arachidonic acid is esterified in membrane phospholipids where its presence is tightly regulated through multiple interconnected pathways. Free arachidonic acid is a transient, critical substrate for the biosynthesis of eicosanoid second messengers. Receptor-stimulated release, metabolism, and re-uptake of free arachidonate are all important aspects of cell signaling and inflammation.

The present invention is directed to a dietary composition for a companion animal comprising polyunsaturated fatty acid comprising 20 or more carbons; and a botanical.

The term "botanical" refers to a substance obtained from a plant and used as an additive in a composition. Under one embodiment, the term "botanical" refers to food or a dietary supplement extracted or derived from a plant or an herbal source. Under one embodiment, the term refers to a food or a dietary supplement extracted or derived from a plant or herbal source that can provide health benefits, such as treating a disease or a health condition, or preventing a disease or a health condition.

Examples of a botanical include substances derived from curcumin, green tea, pomegranate, chamomile, rosemary, aloe, nettle, *Centella asiatica, Ginkgo biloba, Betula,* witch hazel, grape skin, grape seed, grapefruit, grapefruit seed, bilberry, blueberry, soy isoflavones, black cohosh, St. John's wort, *echinacea,* and chamomile. A botanical may be extracted or derived from sources such as acai, aloe vera, Asian *ginseng, astragalus,* bilberry, bitter orange, black cohosh, butterbury, cat's claw, chamomile, chasteberry, cinnamon, cranberry, candelion, *echinacea,* ephedra, European elder, European mistletoe, evening primrose oil, fenugreek, feverfew, flaxseed and flaxseed oil, garlic, ginger, *ginkgo,* goldenseal, grape seed extract, green tea, hawthorn, hoodia, horse chestnut, kava, lavender, licorice root, milk thistle, noni, passionflower, peppermint oil, red clover, sage, saw palmetto soy, St. John's wort, tea tree oil, thunder god vine, turmeric, valerian, and yohimbe.

Under one embodiment, the present invention is directed to a dietary composition for a companion animal comprising greater than about 0.10 wt % of polyunsaturated fatty acid comprising 20 or more carbons; and a botanical selected from the group consisting of licorice root, *angelica* root, fenugreek, marigold, fennel, peppermint leaf, chamomile, dandelion, savory, green tea, tulsi, basil, alfalfa, parsley, fennel, goldenseal, and mixtures thereof.

For each of the plants above, the botanical may derived from one or more parts of the plant.

Further, the botanical may be an extract of such plants. An extract of a plant as used herein is any preparation containing substances extracted from said plant, including fluid extracts, tinctures, essential oils, distillates and oleoresins. Extracts of a plant may be prepared by any of the methods described herein or as known in the art by a skilled worker. Examples of extracts include chamomile extracts, grape skin extract, grape seed extract, grapefruit extract, grapefruit seed extract, bilberry extract, and blueberry extract.

The term "licorice" refers to the plant *Glycyrrhiza glabra* and derivatives thereof. Licorice is an herb that is native to the Mediterranean, southern and central Russia, Asia Minor, and Iran, but is now grown throughout Europe, Asia, and the Middle East. By way of example, licorice may include products derived from the leaves, stems, seeds, and roots of a licorice plant. Licorice may be in the form of a ground powder, freshly ground, spray dried, freeze dried, wet root, extract, oil, suspension, oil and water, or solution. Licorice may be cooked or raw. Many species licorice root for companion animals is thought to be beneficial for numerous health challenges the companion animal may experience. Licorice root contains glycyrrhizin that has similar properties to the adrenal cortex hormones such as cortisol, thus licorice root may display significant anti-inflammatory effects that can be beneficial in instances of arthritis or allergies. Licorice root may also act as an anti-hepatotoxic that can inhibit injury to the liver due to toxins and viruses making this formula a good choice in instances of high liver enzymes resulting from acute or chronic hepatitis. The definition of the phrase "licorice root" includes compositions comprising glycyrrhizin, and composition that are deglyrrhizinated.

*Angelica* refers to any of about 60 species of tall biennial and perennial herbs in the family Apiaceae. *Angelica* is a tall, stout woody perennial that thrives best in slightly acidic, damp soil in light shade. It is native of Syria, but has spread to many European countries. By way of example, *angelica* may include products derived from the leaves, stems, seeds, and roots of any of the *angelica* plant. *Angelica* may be in the form of a ground powder, freshly ground, spray dried, freeze dried, wet root, extract, oil, suspension, oil and water, or solution. *Angelica* may be cooked or raw. The roots have high levels of terpenes, including α-pinene and β-phellandrene.

Fenugreek refers to the plant *Trigonella* foenum-graecum, an annual plant in the family Fabaceae. Fenugreek is an annual plant cultivated worldwide as a semiarid crop. By way of example, fenugreek may include products derived from the leaves, stems, seeds, and roots of a fenugreek plant. Fenugreek may be in the form of a ground powder, freshly ground, spray dried, freeze dried, wet root, extract, oil, suspension, oil and water, or solution. Fenugreek may be cooked or raw. Fenugreek is used as a common spice, particularly in India and places that ingest curries. Traditional medicine practitioners have considered fenugreek to be useful for management of metabolic and nutritive disorders such as diabetes, as a phlegm mover, digestion promoter, labor inducer, and useful in breaking up stuck energies and cool inflammation.

Marigold is a short-lived aromatic and herbaceous perennial native to southern Europe. Under one embodiment the term "marigold" refers to *Calendula officinalis.* Under one embodiment the term "marigold" refers to the genus *Calendula* of the Asteraceae family. The marigold blooms in vivid yellow, orange, and gold colors. By way of example, marigold may include products derived from the leaves, stems, seeds, and roots of a ginger plant. Marigold may be in the form of a ground powder, freshly ground, spray dried, freeze dried, wet root, extract, oil, suspension, oil and water, or solution. The marigold may be cooked or raw. Marigold extract is a commonly in pet food due to its anti-microbial and anti-inflammatory properties. It can aid in digestion and reduce inflammation and combat viruses and bacteria. The flavonoids in the extract can add flavor and is also a source of plant antioxidants. Marigold contains large amounts of lutein which is found in the retina of the eye. Lutein protects the eye from the development of cataracts and macular degeneration.

Fennel refers to the plant *Foeniculum vulgare* and derivatives thereof. Native to the Mediterranean, fennel is now found throughout the world. Fennel is a perennial, aromatic herb with yellow flowers and a bulb like stem. By way of example, fennel may include products derived from the leaves, stems, seeds, and roots of a fennel plant. Fennel may be in the form of a ground powder, freshly ground, spray dried, freeze dried, wet root, extract, oil, suspension, oil and water, or solution. The fennel may be cooked or raw. Fennel has a similar smell to licorice or anise. Fennel is added to pet food as a source of several key vitamins, or as a digestive aid.

Peppermint is a hybrid mint, a cross between watermint and spearmint, and is indigenous to Europe and the Middle East. Oil from peppermint has a high menthol content. and also contains menthone, carboxyl esters, such as menthyl acetate. Peppermint oil also contains small amounts of many additional compounds including limonene, pulegone, caryophyllene and pinene. Peppermint contains terpenoids and flavonoids such as eriocitrin, hesperidin, and kaempferol 7-O-rutinoside. Peppermint helps manage peristalsis in pets, meaning it regulates the contractions that help move food along their digestive tracts. Giving your pet a little peppermint can help improve irritable bowel syndrome. When paired with catnip, peppermint can reduce nausea in companion animals as well.

Chamomile refers to any one of several daisy-like plants of the family Asteraceae, and derivatives thereof. Under one embodiment, chamomile refers to the plant *Matricaria chamomilla* and derivatives thereof. Under one embodiment, chamomile refers to the plant *Chamaemelum nobile* and derivatives thereof. By way of example, chamomile may include products derived from the leaves, stems, seeds, and roots of a chamomile plant. Chamomile may be in the form of a ground powder, freshly ground, spray dried, freeze dried, wet root, extract, oil, suspension, oil and water, or solution. The chamomile may be cooked or raw.

Dandelion refers to any one of several flowering plants in the *taraxacum* genus and derivatives thereof. Dandelion are flowering plants native to Eurasia and North America. Several species of dandelion, including the leaves, stems, flowers, and roots, are edible and nutritious. By way of example, dandelion may include products derived from the leaves, stems, seeds, and roots of a dandelion plant. Dandelion may be in the form of a ground powder, freshly ground, spray dried, freeze dried, wet root, extract, oil, suspension, oil and water, or solution. The dandelion may be cooked or raw. Dandelion leaves contain abundant vitamins and minerals, especially vitamins A, C, and K, and are good sources of calcium, potassium, iron, and manganese. The raw flowers contain high levels of polyphenols and antioxidants, and are anti-inflammatory and anti-angiogenic.

Savory refers to the plant *satureja*, a genus of aromatic plants of the family Lamiaceae, related to rosemary and thyme, and derivatives thereof. By way of example, savory may include products derived from the leaves, stems, seeds, and roots of a savory plant. Savory may be in the form of a ground powder, freshly ground, spray dried, freeze dried, wet root, extract, oil, suspension, oil and water, or solution. The savory may be cooked or raw.

Green tea originates from the plant species *Camellia sinensis*. Green tea is considered to have originated in China's Yunnan province Green tea considered an excellent source of antioxidants and alkaloids, containing vitamins, such as A, D, E, C, B, B5, H and K, manganese and other minerals such as zinc, chromium and selenium. Green tea is about 30 percent polyphenols by weight, including large amounts of a catechin EGCG. Catechins are natural antioxidants that are thought to help prevent cell damage.

Tulsi refers to the plant *Ocimum tenuiflorum* and derivatives thereof. Tulsi is also known as holy basil, tulasi, or thulasi. Tulsi is an aromatic perennial plant in the family Lamiaceae, native to the Indian subcontinent and widespread as a cultivated plant throughout the Southeast Asian tropics. By way of example, tulsi may include products derived from the leaves, stems, seeds, and roots of a tulsi plant. Tulsi may be in the form of a ground powder, freshly ground, spray dried, freeze dried, wet root, extract, oil, suspension, oil and water, or solution. The tulsi may be cooked or raw. Some of the phytochemical constituents of tulsi are oleanolic acid, ursolic acid, rosmarinic acid, eugenol, carvacrol, linalool, and β-caryophyllene. Tulsi essential oil consists mostly of eugenol, β-elemene, β-caryophyllene, and germacrene.

Basil refers to the plant *Ocimum basilicum* and derivatives thereof. Basil is native to tropical regions from central Africa to Southeast Asia, and is used in cuisines worldwide. By way of example, basil may include products derived from the leaves, stems, seeds, and roots of a basil plant. Basil may be in the form of a ground powder, freshly ground, spray dried, freeze dried, wet root, extract, oil, suspension, oil and water, or solution. Basil may be cooked or raw. In traditional medicine practices, such as those of Ayurveda or traditional Chinese medicine, basil is thought to have therapeutic properties.

Alfalfa refers to the plant *Medicago sativa* and derivatives thereof. Alfalfa also named lucerne, is a perennial flowering plant in the legume family Fabaceae. It is cultivated as an important forage crop in many countries around the world. It is used for grazing, hay, and silage, as well as a green manure and cover crop. By way of example, alfalfa may include products derived from the leaves, stems, seeds, and roots of a alfalfa plant. Alfalfa may be in the form of a ground powder, freshly ground, spray dried, freeze dried, wet root, extract, oil, suspension, oil and water, or solution. Alfalfa may be cooked or raw.

Parsley refers to the plant Petroselinum crispum and derivatives thereof. Parsley is a biennial is a species of flowering plant in the family Apiaceae, native to the central Mediterranean region, and widely cultivated as an herb, a spice, and a vegetable. By way of example, parsley may include products derived from the leaves, stems, seeds, and roots of a parsley plant. Parsley may be in the form of a ground powder, freshly ground, spray dried, freeze dried, wet root, extract, oil, suspension, oil and water, or solution. Parsley may be cooked or raw.

Goldenseal refers to the plant Hydrastis *canadensis* and derivatives thereof, is a perennial herb in the buttercup family Ranunculaceae, native to southeastern Canada and the eastern United States. By way of example, goldenseal may include products derived from the leaves, stems, seeds, and roots of a goldenseal plant. Goldenseal may be in the form of a ground powder, freshly ground, spray dried, freeze dried, wet root, extract, oil, suspension, oil and water, or solution. Goldenseal may be cooked or raw. In traditional medicine, goldenseal's roots and rhizomes are harvested and used as a multi-purpose remedy because of their high concentrations of berberine and hydrastine. The herb is believed to be anti-inflammatory, anti-diarrheal, antibacterial and immune-enhancing. Goldenseal is used to control muscle spasms, treat cancer, stimulate the heart and increase blood pressure, treat gastrointestinal disorders, treat conjunctivitis, manage painful and heavy menstruation, treat infections topically, reduce swelling and alleviate edema.

The composition of the present invention may be prepared by any means of preparing pet food. Arachidonic acid may be obtained commercially from any number of sources. It may be prepared from the fungus *Mortierella alpina*.

The composition of the invention can be a liquid or a solid food. Where the composition is a liquid, polyunsaturated fatty acid comprising 20 or more carbons, and the botanical, can be admixed with other components. Where the composition is a solid, the polyunsaturated fatty acid comprising 20 or more carbons, and the botanical, may be coated on the composition, or incorporated into the composition or both.

In various embodiments, the polyunsaturated fatty acid comprising 20 or more carbons, and the botanical, may be added to the companion animal's food. In certain embodiments, the polyunsaturated fatty acid comprising 20 or more carbons, and the botanical, may be added to the companion animal's food by a compounder or manufacturer at a site. In a certain embodiment, the polyunsaturated fatty acid comprising 20 or more carbons, and the botanical, may be added to a companion animal's food by the companion animal's caregiver prior to feeding the animal. In other embodiments, the polyunsaturated fatty acid comprising 20 or more carbons, and the botanical, may be added during the processing of a companion animal's food, such as during and/or after mixing of other components of the composition that is then packaged and made available to consumers. Such processing may include extrusion, canning, baking and the like or any other method of process of producing pet foods that is known in the art.

As contemplated herein, the compositions of the present invention are meant to encompass nutritionally complete and balanced animal feed compositions that additionally comprise the polyunsaturated fatty acid comprising 20 or more carbons, and the botanical. A "nutritionally complete diet" is a diet that includes sufficient nutrients for maintenance of normal health of a healthy companion animal on said diet.

Nutritionally complete and balanced pet food compositions are understood by a person of ordinary skill in the art. For example, substances such as nutrients and ingredients suitable for nutritionally complete and balanced animal feed compositions, and recommended amounts thereof, may be found for example, in the Official Publication of The Association of American Feed Control Officials, Inc. (AAFCO). Atlanta, Ga., 2005, or the National Research Council's Nutrient Requirements of Dogs and Cats, The National Academy Press, Washington, D.C., 2006.

As used herein, an "ingredient" refers to any component of a composition. The term "nutrient" refers to a substance that provides nourishment. In some cases an ingredient may comprise more than one "nutrient". The distinction in these terms is familiar to one of skill in the art.

A nutritionally complete and balanced dog food composition of the present invention may comprise: about 0 wt % to about 90 wt %, preferably about 5 wt % to 60 wt % of carbohydrates; about 5 wt % to about 70 wt %, preferably about 10 wt % to about 60 wt % of protein; about 2 wt % to about 50 wt %, preferably about 5 wt % to about 40 wt % of fat; about 0.1 wt % to about 20 wt %, preferably about 1 wt % to about 11 wt % of total dietary fiber; about 0 wt % to about 15 wt %, preferably about 2 wt % to about 8 wt % of vitamins and minerals, antioxidants, and other nutrients which support the nutritional needs of the animal; about 0.1 wt % to about 3 wt %, or about 0.1 wt % to about 1.5 wt %, or about 0.1 wt % to about 0.6 wt % of polyunsaturated fatty acid comprising 20 or more carbons; and about 0.0010 wt % to about 1.0 wt % botanical, or about 0.0010 wt % to about 0.01 wt % botanical.

For example, a nutritionally complete and balanced cat food composition of the present invention may comprise: about 0 to about 90%, preferably about 5% to 50%, by weight of carbohydrates; about 5% to about 70%, preferably about 20% to about 60%, by weight of protein; about 2% to about 50%, preferably about 5% to about 40%, by weight of fat; about 0.1% to about 20%, preferably about 1% to about 11%, by weight of total dietary fiber; about 0 to about 15%, preferably about 2% to about 8%, by weight of vitamins and minerals, antioxidants, and other nutrients which support the nutritional needs of the animal; about 0.1 wt % to about 3 wt %, or about 0.1 wt % to about 1.5 wt %, or about 0.1 wt % to about 0.6 wt % of polyunsaturated fatty acid comprising 20 or more carbons; and about 0.0010 wt % to about 1.0 wt % botanical, or about 0.0010 wt % to about 0.01 wt % botanical.

Under one embodiment, the present invention is directed to a dietary composition for a companion animal comprising greater than about 0.10 wt % of polyunsaturated fatty acid comprising 20 or more carbons; and a botanical, wherein the botanical is selected from the group consisting of green tea, fenugreek, tulsi, and mixtures thereof. The botanical may be green tea, or fenugreek, or tulsi, or green tea and fenugreek, or green tea and tulsi, or fenugreek and tulsi, or green tea, fenugreek and tulsi. Further, the botanical may be green tea mixed with other botanicals; or fenugreek mixed with other botanicals; or tulsi mixed with other botanicals; or green tea and fenugreek, mixed with other botanicals; or green tea and tulsi, mixed with other botanicals; or fenugreek and tulsi, mixed with other botanicals; or green tea, fenugreek and tulsi, mixed with other botanicals.

Under one embodiment, the present invention is directed to a dietary composition for a companion animal comprising greater than about 0.10 wt % of polyunsaturated fatty acid comprising 20 or more carbons; and a botanical comprising a mixture of green tea, fenugreek, and tulsi. Under this embodiment, all three botanicals are necessarily present in dietary composition. Further, under an embodiment, other botanicals in addition to green tea, fenugreek, and tulsi, may be present.

The green tea, fenugreek, and tulsi may be present in any amount that is effective in treating inflammation in a companion animal. Under one embodiment each of the green tea, fenugreek, and tulsi is present in the composition at greater than about 0.0010 wt %. Under one embodiment the dietary composition comprises greater than about 0.20 wt % green tea, greater than about 0.020 wt % fenugreek, and greater than about 0.0010 wt % tulsi.

The efficacy of anti-inflammatory substance, such as pet food, may be measured directly by monitoring inflammation. Alternatively, the efficacy of anti-inflammatory substance may be measured by the reduction of selected circulating pro-inflammatory cytokines in the companion animal. Suitable pro-inflammatory cytokines include TNFα, MCP-1, IL12 and IL18.

Tumor necrosis factor (TNFα) is a pro-inflammatory protein that is mainly produced by activated macrophages. They can also be produced by CD4 lymphocytes, NK cells, neutrophils, mast cells, and eosinophils. Reducing TNFα has been shown to reduce inflammatory responses in several disease conditions including glomerulonephritis, intestinal bowel disorders, and dermatitis.

Monocyte chemoattractant protein 1 (MCP-1) is also referred to as chemokine ligand 2 (CCL2). MCP-1 recruits monocytes, memory T cells, and dendritic cells to the site of injury but does not attract neutrophils or eosinophils. Anti-CCl2 reduces severity of renal dysfunction (glomerulone-phritis) indicating that a reduction of MCP-1 is beneficial in restoring renal function.

Interleukin 12 (IL-12) is a pro-inflammatory cytokine that is produced mainly by dendritic cells and macrophages. IL-12 is involved in the differentiation of naïve T cells to Th1 cells and also stimulates the production of pro-inflammatory TNFα and interferon gamma (IFNγ). IL12 also stimulates production of natural killer cells (NK cells) and enhances the cytotoxic activity of NK cells and CD8 cytotoxic T cells.

Interleukin-18 (IL-18) is a cytokine that is produced primarily by macrophages. One of the pro-inflammatory actions of IL-18 is due to its ability to stimulate NK cells and certain T cells to release IFNg.

Previous studies have suggested that an addition of arachidonic acid to pet food would be pro-inflammatory. However, the feeding of cats cat food comprising added arachidonic acid did not significantly change of the levels of the TNFα, MCP-1, or IL-18.

Other previous studies have suggested that an addition of botanicals to pet food would be anti-inflammatory. However, the feeding of cats cat food comprising botanicals did not significantly change of the levels of the TNFα, MCP-1, or IL-18.

However, feeding cats a combination of arachidonic acid and botanicals in pet food has shown very significant anti-inflammatory effect as exhibited by the reduction of TNFα, MCP-1, and IL-18.

EXAMPLES

A two-factor, two-level experiment was performed. The first factor was the presence or absence of a botanical mixture. The second factor was the presence or absence of additional arachidonic acid over the natural presence of the acid in the food.

Forty-eight cats were divided into four groups of twelve cats in each group. The cats in the control group (Group 1) were fed a nutritionally balanced cat food. The cats in the botanical only group (Group 2) were fed the nutritionally balanced cat food to which a botanical complex was added. The cats in the arachidonic acid only group (Group 3) were fed the nutritionally balanced cat food to which arachidonic acid was added. The cats in the arachidonic acid-botanical complex group (Group 4) were fed the nutritionally balanced cat food to which arachidonic acid and a botanical complex were added.

The cat food of Groups 2 and 4 each contained 0.5 wt % of green tea, 0.05 wt % of fenugreek, and 0.003 wt % tulsi.

The cat food of Groups 1 and 2 contained about 0.05 wt % to 0.06 wt % of arachidonic acid that naturally occurs in meat product in the cat food. The cat food of Groups 3 and 4 each contained addition arachidonic acid that was mixed in, to yield about 0.13 wt % of the arachidonic acid.

Each group was fed its respective diet for 85 days, after which, the inflammatory status of the was cats evaluated, using specific cytokines as the measure of inflammatory response.

TABLE 1

| Group | Δ TNFα, LS(mean) | Standard error | Pr > \|t\| |
|---|---|---|---|
| 1 | −64.78 | 80.2 | 0.4237 |
| 2 | −0.3992 | 80.2 | 0.9961 |
| 3 | 54.21 | 80.2 | 0.5028 |
| 4 | −243.6 | 80.2 | 0.0040 |
| Group | Δ IL18 LS(mean) | Standard error | Pr > \|t\| |
| 1 | −179.3 | 286.0 | 0.5339 |
| 2 | 100.8 | 286.0 | 0.7262 |
| 3 | 140.67 | 286.0 | 0.6253 |
| 4 | −756.7 | 286.0 | 0.0113 |
| Group | Δ MCP1 LS(mean) | Standard error | Pr > \|t\| |
| 1 | 34.83 | 434.3 | 0.9364 |
| 2 | −322.14 | 434.3 | 0.4622 |
| 3 | 371.87 | 434.3 | 0.3965 |
| 4 | −1345.1 | 434.3 | 0.0034 |

As illustrated in Table 1 (above), there was a statistically significant decrease in the amounts of each of the cytokines. The p-value (single tailed) for the decrease of TNFα was less than 0.5%. The p-value (single tailed) for the decrease of IL 18 was less than 0.12%. The p-value (single tailed) for the decrease of MCP1 was less than 0.4%.

While the present invention has been described with reference to several embodiments, which embodiments have been set forth in considerable detail for the purposes of making a complete disclosure of the invention, such embodiments are merely exemplary and are not intended to be limiting or represent an exhaustive enumeration of all aspects of the invention. The scope of the invention is to be determined from the claims appended hereto. Further, it will be apparent to those of skill in the art that numerous changes may be made in such details without departing from the spirit and the principles of the invention.

The invention claimed is:

1. A pet food composition comprising:
greater than about 0.10 wt % to about 1.5 wt % of arachidonic acid; and
a botanical blend comprising greater than about 0.20 wt % green tea, greater than about 0.020 wt % fenugreek, and greater than about 0.0010 wt % tulsi,
wherein all wt % are with respect to the pet food composition on a dry matter basis.

2. The pet food composition of claim 1, further comprising a polyunsaturated fatty acid selected from the group consisting of eicosadienoic acid, eicosatrienoic acid, eicosatetraenoic acid, docosadienoic acid, docosatetraenoic acid, docosapentaenoic acid, tetracosatetraenoic acid, tetracosapentaenoic acid, and mixtures thereof.

3. The pet food composition of claim 1, wherein the botanical blend further comprises a botanical selected from the group consisting of licorice root, angelica root, marigold, fennel, peppermint leaf, chamomile, dandelion, savory, basil, alfalfa, parsley, goldenseal, and mixtures thereof.

4. The pet food composition of claim 1, wherein the botanical blend consists of a mixture of green tea, fenugreek, and tulsi.

5. The pet food composition of claim 1, wherein the pet food composition is a nutritionally complete pet food.

6. The pet food composition of claim 1, further comprising:
a nutritionally complete carrier; and
an effective amount of an anti-inflammatory complex, the anti-inflammatory complex comprising:
the botanical blend; and
the arachidonic acid.

7. The pet food composition according to claim 6, wherein the composition provides a synergistic reduction in one or more inflammatory cytokines.

8. The pet food composition according to claim 7, wherein the inflammatory cytokines are selected from TNFα, IL 18, MCP1, and combinations thereof.

9. The pet food composition according to claim 1, wherein the arachidonic acid is present in an amount of greater than about 0.10 wt % to about 0.6 wt %.

\* \* \* \* \*